United States Patent [19]

Pilone

[11] Patent Number: 5,948,660
[45] Date of Patent: Sep. 7, 1999

[54] DNA FRAGMENT ENCODING D-AMINO ACID OXIDASE

[76] Inventor: Mirella Pilone, Via Pontaccio 10, Milan, Italy

[21] Appl. No.: 08/732,461

[22] PCT Filed: Mar. 4, 1996

[86] PCT No.: PCT/EP96/00905

§ 371 Date: Nov. 4, 1996

§ 102(e) Date: Nov. 4, 1996

[87] PCT Pub. No.: WO96/27667

PCT Pub. Date: Sep. 12, 1996

[30] Foreign Application Priority Data

Mar. 7, 1995 [IT] Italy ................................ MI95A0442

[51] Int. Cl.$^6$ ............................ C12N 15/53; C12N 15/11; C12N 15/70; C12N 9/06
[52] U.S. Cl. .................... 435/191; 435/69.1; 435/252.3; 435/320.1; 536/23.2; 536/24.3
[58] Field of Search .................... 435/69.1, 189, 435/252.3, 320.1; 536/23.2, 24.3

[56] References Cited

U.S. PATENT DOCUMENTS

| | | | |
|---|---|---|---|
| 4,652,639 | 3/1987 | Stabinsky | 536/27 |
| 5,424,196 | 6/1995 | Cambiaghi et al. | 435/51 |
| 5,434,058 | 7/1995 | Davidson | 435/69.1 |
| 5,453,374 | 9/1995 | Furuya et al. | 435/254.11 |
| 5,459,037 | 10/1995 | Sutcliffe et al. | 435/6 |
| 5,541,110 | 7/1996 | Siegall | 435/252.3 |
| 5,550,037 | 8/1996 | Francavilla et al. | 435/69.1 |
| 5,565,323 | 10/1996 | Parker et al. | 435/6 |
| 5,602,016 | 2/1997 | Isogai et al. | 435/189 |
| 5,627,264 | 5/1997 | Fodor et al. | 530/350 |
| 5,741,898 | 4/1998 | Hanley et al. | 536/23.2 |

FOREIGN PATENT DOCUMENTS

| | | |
|---|---|---|
| 0 496 993 | 8/1992 | European Pat. Off. . |
| 0 583 817 | 2/1994 | European Pat. Off. . |

OTHER PUBLICATIONS

Simonetta, M.P., et al., FEMS Microbiology Letters, vol. 15, "D–Amino acid oxidase activity in the yeast *Rhodotorula gracilis*", pp. 27–31, 1982.

Simonetta, M.P., et al., Journal of General Microbiology vol. 135, "Induction of D–Amino acid Oxidase by D–Alanine in *Rhodotorula gracilis* Grown in Defined Medium", pp. 593–600, 1984.

Fortkamp, E., et al., DNA, vol. 5, "Cloning and expression in *Escherichia coli* of a Synthetic DNA for Hirudin, the Blood Coagulation Inhibitor in the Leech", pp. 511–517, 1986.

Anson, J.G., et al., Gene, vol. 58, "Complete nucleotide sequence of the *Rhodospordium, toruloides* gene coding for phenylalanine ammonia–lyase", pp. 189–199, 1987.

Pilone, M.S., et al., Biotechnology Letters, vol. 17, "A process for bioconversion of cephalosporin C by *Rhodotorula gracilis* D–amino acid oxidase", pp. 199–204, 1995.

Biotechnol. Lett (1995), 17(2), 193–8, "The primary structure of D–amino acid oxidase from *Rhodotorula gracilis*", Ludovica Faotto et al.

Biochemistry, vol. 26, No. 12, Jun. 16, 1987, pp. 3612–3618, Molecular Cloning and Sequence Analysis of cDNAs Encoding Porcine Kidney D–Amino Acid Oxidase, K. Fukui et al.

Chemical Abstracts, vol. 124, No. 5, Jan. 29, 1996, Abstract No. 49325, "Amino acid sequence of D–amino oxidase from the yeast *Rhodotorula gracilis*", Ludovica Faotto et al.

Chemical Abstracts, vol. 124, No. 7, Feb. 19, 1996, Abstract No. 80208, "Simple and rapid determinations of the activity of recombinant D–amino acid oxidase etc.", In–wook Kim et al.

*Primary Examiner*—Ponnathapura Achutamurthy
*Assistant Examiner*—William W. Moore
*Attorney, Agent, or Firm*—Griffin, Butler, Whisenhunt & Szipl

[57] ABSTRACT

The invention relates to a DNA fragment encoding the gene for D-amino acid oxidase, a method for the preparation of said fragment and the uses of the enzyme expressed by said fragment.

7 Claims, No Drawings

DNA FRAGMENT ENCODING D-AMINO ACID OXIDASE

The preparation of 7-aminocephalosporanic acid is carrier out according to the following scheme:

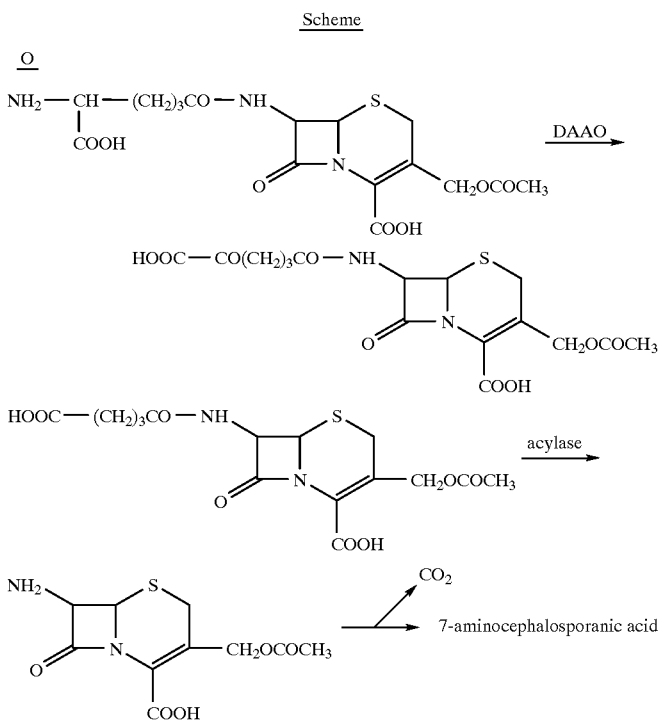

The instant application is a national stage filing under 35 U.S.C. §371 of PCT application PCT/EP 96/00905, filed Mar. 4, 1996.

The present invention relates to the biotechnology field, particularly a DNA fragment encoding a D-amino acid oxidase enzyme.

FIELD OF THE INVENTION

There is a long standing interest towards the enzyme D-amino acid oxidase (E.C. 1.4.3.3, DAAO) due to its possible applications in the pharmaceutical and therapeutical fields.

Said enzyme catalyzes the conversion of D-amino acids into the corresponding α-keto acids.

α-Keto acids are important therapeutical agents useful in the treatment of chronic uraemia (Mackenzie Walser, M.D., Am. J. Cl. Nutr. 31, 1756–1760 (1978)).

D-amino acid oxidase (hereinbelow defined DAAO for the sake of brevity), obtained from the yeast *Rhodotorula gracilis*, has been used efficiently for the production of keto derivatives in a reactor system (Buto', S. et al., Biotech. Bioeng., 44, 1288–1294 (1994)).

Furthermore, the same enzyme exhibited a high activity on cephalosporin C (Pilone, M. S. et al., Biotech. Appl. Biochem., 16, 252–262 (1992) and it can be exploited in the production of 7-aminocephalosporanic acid, which is a key intermediate in the industrial production of semisynthetic cephalosporins.

The activity on the antibiotic substrate cephalorosporin C is much higher than other reported activities of DAAO. (Pilone, ibid.).

Another application of the enzyme DAAO isolated from *Rhodotorula gracilis* is its use in the oxidative therapy for the treatment of tumors; DAAO can be used as a promising enzyme system for the generation of oxygen-reactive species for the in situ treatment of tumors, mainly brain tumors (Ben Yoseph, O. et al. British J. Cancer (1995)). Such an oxidase activity is more interesting than others due to its non-physiological substrate (D-amino acids).

The genetics of the yeast *Rhodotorula gracilis* is still completely unknown and, though DAAO produced therefrom has been extensively characterized in its kinetic and functional aspects (Pollegioni, L. et al., J. Biol. Chem., 268, 13580 135887 (1993)), no information at all were reported about a gene encoding for protein.

The availability of the above sequence encoding the DAAO will allow for the ingegnerization of the protein, thus giving higher yields and improved characteristics.

DISCLOSURE OF THE INVENTION

Now it has been found, and it is the object of the present invention, a deoxyribonucleic acid (DNA) fragment encoding the gene for D-amino acid oxidase of the yeast *Rhodotorula gracilis*.

The DNA fragment according to the present invention has the sequence Id n. 1.

The present invention also relates to the functional analogues of said sequence. By functional analogues, degenerated sequences, allelic variants and mutant sequences are meant.

Another object of the present invention is a method for the preparation of said DNA fragment.

According to the present invention said method comprises:
a) culture of a *Rhodotorula gracilis* strain in conditions inducing D-amino acid oxidase;
b) purification of the total fraction of mRNA specific for said D-amino acid oxidase;
c) synthesis of a first cDNA strand;
d) amplification of said cDNA strand by means of the technique known as Polymerase Chain Reaction (PCR), wherein the following synthetic oligonucleotides are used as specific primers:

5'-TCC AAG AAT TCG CGG CCG-3' Sequence Id n. 2 (I)

5'-ATG CAC TCG CAG AAG CGC GTC-3' Sequence Id n. 3 (II)

to give said DNA fragment;
e) cloning of said fragment in a suitable plasmid;
f) isolation of said fragment.

In a first embodiment of the invention, the yeast *Rhodotorula gracilis* is the strain PAN, ATCC 26217.

The DAAO induction is carried out by conventional methods, disclosed in Pilone, S. et al., J. Gen. Microbiol., 135, 593–600, (1989).

The messenger ribonucleic acid (mRNA) total fraction was purified by conventional techniques, according to Maniatis et al., Molecular Cloning: A Laboratory manual, Cold Spring Harbor Laboratory, (1992).

In a preferred embodiment of the present invention, the synthesis of the cDNA strand is effected using a Moloney Murine Leukemia Virus reverse transcriptase and a notI-d $(T)_{18}$ synthetic oligonucleotide having the following sequence ID n. 4 (5'd[AAC TGG AAG AAT TCG CGG CCG CAG GAA $T_{18}$]-3'. Both the transcriptase and the synthetic oligonucleotide are commercially available. The preparation of cDNA is described in Maniatis et al. (ibid.).

The method according to the present invention is characterized in that the specific primers used in the PCR step are those synthetic oligonucleotides reported above (I) and (II). Said synthetic oligonucleotides, defined respectively notI and DAAOn, have been found in the partial protein sequence of DAAO purified from *Rhodotorula gracilis* (notI) and the codon usage deriving from the phenylalanine ammonia-lyase gene of *Rhodosporidium toruloides* (DAAOn), the latter being described by Gilbert, H. J. et al., J. Bacteriol., 161, 314–320, (1985).

The plasmid in which the DNA fragment from PCR is cloned is a conventional vector used for this kind of procedures, for example the plasmid pCR II by Invitrogen.

The isolation and sequencing of the DNA fragment of the present invention are carried out according to conventional methods known to those skilled in the art, for example as described in the above mentioned Maniatis et al.

The following example further illustrate the invention.

EXAMPLE

*Rhodotorula gracilis*, strain PAN ATCC 26217, was grown in DAAO-inducing conditions, using a culture medium at pH 5.6 containing 30 mM D-alanine, as described in Pilone, S. et al., J. Gen. Microbiol., 135, 593–600, (1989), to obtain the maximum amount of specific DAAO mRNA.

The mRNA total fraction was purified by affinity chromatography on an oligo-dT cellulose column (see Maniatis et al., ibid.). This sample was used for the preparation of a first strand of CHEDDAR, employing a Moloney Murine Leukemia Virus reverse transcriptase and a synthetic oligonucleotide notI-d$(T)_{18}$, having the following sequence (Sequence ID n. 4).

(5'-d[AAC TGG AAG AAT TCG CGG CCG CAG GAA $T_{18}$]-3' as the primer.

The single strand CHEDDAR was used for specific PCR amplification reaction using, as specific primers, synthetic oligonucleotides designed from the partial protein sequence of the purified DAAO from *Rhodotorula gracilis* and the codon usage derived from the phenylalanine ammonia-lyase gene of *Rhodosporidium toruloides* (Gilbert et al., ibid). For the amplification of the total fragment of the gene encoding DAAO the following oligonucleotides were used:

notI 5'-TCC AAG AAT TCG CGG CCG-3' Sequence Id n. 2

DAAOn 5'-ATG CAC TCG CAG AAG CGC GTC-3' Sequence Id n. 3

The amplification conditions were:

94° C.×60"

35×(94° C.×60"

65° C.×50"

72° C.×60")

72° C.×10'.

The PCR product resulted in a 1.1 kb DNA fragment and was cloned in a commercial plasmid specific for PCR products (pCR II, Invitrogen).

The amplified and cloned DNA fragment was sequence and its sequence corresponds to the total gene sequence of the gene encoding DAAO from *Rhodotorula gracilis*.

This DNA fragment was excised from the cloning plasmid pCR II using the corresponding EcoRI sites and inserted into a pKK223-3 commercial plasmid (Pharmacia Biotech) linearized by means of the restriction enzyme EcoRI.

The recombinant plasmid was used to transform competent JM105 *E. coli* cells. The expression of the protein product of the cloned D-amino acid oxidase gene was obtained with a IPTG (isopropyl β-D-thiogalactopyranoside) induction of transformed *E. coli* cells by addition of 1 mM IPTG (final concentration) to a cell culture in exponential growth ($E_{600}$=0.8) conditions.

The cells were grown for additional 6 hours at 37° C. before harvesting at 7000 x g. The cell paste was sonicated 4 times for 1 min and the cell extract partially purified according to Pollegioni and Pilone (Prof. Express. Purif. 3, 165–167, (1992)). The protein sample was separated by SDS-PAGE electrophoresis under denaturing conditions and the protein band with a molecular weight of 40 kDA was electrotransferred to a polyvinylidene difluoride membrane, stained and directly used for sequencing analysis. The N-terminal sequence (10 residues determined) corresponds to the primary sequence of the D-amino acid oxidase protein purified from *R. gracilis*:

Met-His-Ser-Gln-Lys-Arg-Val-Val-Val-Leu (SEQ. ID NO.: 5)

The present invention also relates to the plasmids containing the fragment of the gene encoding the DAAO of *Rhodotorula gracilis*.

I claim:

1. An isolated DNA fragment having the nucleotide sequence set forth in SEQ ID NO: 1 and encoding D-amino acid oxidase from the yeast *Rhodotorula gracilis*.

2. A method for the preparation of the DNA fragment of claim 1, comprising:
   a) culturing a *Rhodotorula gracilis* strain in conditions inducing D-amino acid oxidase;
   b) purifying the total fraction of mRNA specific for said D-amino acid oxidase;
   c) synthesizing a first cDNA strand;
   d) amplifying said cDNA strand by means of the technique known as Polymerase Chain Reaction (PCR), wherein oligonucleotides having the sequences set forth in SEQ IDs NOs: 2 and 3 are used as specific primers to give said DNA fragment;
   e) cloning said fragment in a suitable plasmid; and
   f) isolating said fragment from said plasmid.

3. A method according to claim 2, wherein said yeast *Rhodotorula gracilis* is the strain PAN ATCC 26217.

4. A method according to claim 2, wherein the synthesis of said cDNA strand in step c) is obtained by means of the Moloney Murine Leukemia Virus reverse transcriptase and the notI-d(T)$_{18}$ synthetic oligonucleotide primer having the sequence set forth in SEQ ID NO: 4.

5. A method according to claim 2, wherein said plasmid is pCRII.

6. A plasmid containing the nucleotide sequence of claim 1.

7. A method for expressing D-amino acid oxidase from the yeast *Rhodotorula gracilis,* comprising:
   a) inserting the DNA sequence of claim 1 into a conventional plasmid;
   b) transforming a competent microorganism with said plasmid;
   c) culturing said microorganism in conditions inducing D-amino acid oxidase;
   d) isolating said D-amino acid oxidase.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
       (A) LENGTH: 1107 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Rhodotorula gracilis (xi) SEQUENCE DESCRIPTION: SEQ ID NO: 1:

```
ATGCACTCGC AGAAGCGCGT CGTTGTCCTC GGATCAGGCG TTATCGGTCT GAGCAGCGCC      60

CTCATCCTCG CTCGGAAGGG CTACAGCGTG CATATTCTCG CGCGCGACTT GCCGGAGGAC     120

GTCTCGAGCC AGACTTTCGC TTCACCATGG GCTGGCGCGA ATTGGACGCC TTTCATGACG     180

CTTACAGACG GTCCTCGACA AGCAAAATGG GAAGAATCGA CTTTCAAGAA GTGGGTCGAG     240

TTGGTCCCGA CGGGCCATGC CATGTGGCTC AAGGGGACGA GGCGGTTCGC GCAGAACGAA     300

GACGGCTTGC TCGGGCACTG GTACAAGGAC ATCACGCCAA ATTACCGCCC CCTCCCATCT     360

TCCGAATGTC CACCTGGCGC TATCGGCGTA ACCTACGACA CCCTCTCCGT CCACGCACCA     420

AAGTACTGCC AGTACCTTGC AAGAGAGCTG CAGAAGCTCG GCGCGACGTT TGAGAGACGG     480

ACCGTTACGT CGCTTGAGCA GGCGTTCGAC GGTGCGGATT TGGTGGTCAA CGCTACGGGA     540

CTTGGCGCCA AGTCGATTGC GGGCATCGAC GACCAAGCCG CCGAGCCAAT CCGCGGGCAA     600

ACCGTCCTCG TCAAGTCCCC ATGCAAGCGA TGCACGATGG ACTCGTCCGA CCCCGCTTCT     660

CCCGCCTACA TCATTCCCCG ACCAGGTGGC GAAGTCATCT GCGGCGGGAC GTACGGCGTG     720

GGAGACTGGG ACTTGTCTGT CAACCCAGAG ACGGTCCAGC GGATCCTCAA GCACTGCTTG     780

CGCCTCGACC CGACCATCTC GAGCGACGGA ACGATCGAAG GCATCGAGGT CCTCCGCCAC     840

AACGTCGGCT TGCGACCTGC ACGACGAGGC GGACCCCGCG TTGAGGCAGA ACGGATCGTC     900

CTGCCTCTCG ACCGGACAAA GTCGCCCCTC TCGCTCGGCA GGGGCAGCGC ACGAGCGGCG     960

AAGGAGAAGG AGGTCACGCT TGTGCATGCG TATGGCTTCT CGAGTGCGGG ATACCAGCAG    1020

AGTTGGGGCG CGGCGGAGGA TGTCGCGCAG CTCGTCGACG AGGCGTTCCA GCGGTACCAC    1080

GGCGCGGCGC GGGAGTCGAA GTTGTAG                                        1107
```

(2) INFORMATION FOR SEQ ID NO: 2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (xi) SEQUENCE DESCRIPTION: SEQ ID NO: 2:

-continued

```
TCCAAGAATT CGCGGCCG                                              18

(2) INFORMATION FOR SEQ ID NO: 3:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (xi) SEQUENCE DESCRIPTION: SEQ ID NO: 3:

ATGCACTCGC AGAAGCGCGT C                                          21

(2) INFORMATION FOR SEQ ID NO: 4:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (xi) SEQUENCE DESCRIPTION: SEQ ID NO: 4:

AACTGGAAGA ATTCGCGGCC GCAGGAATTT TTTTTTTTTT TTTTT                45

(2) INFORMATION FOR SEQ ID NO: 5:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (iii) HYPOTHETICAL: NO (v) FRAGMENT TYPE: N-terminal (vi) ORIGINAL SOURCE:
         (A) ORGANISM: Rhodotorula gracilis (xi) SEQUENCE DESCRIPTION: SEQ ID NO: 5:

Met His Ser Gln Lys Arg Val Val Val Leu
1               5                   10
```